(12) United States Patent
Sheppard, Jr.

(10) Patent No.: US 6,684,976 B1
(45) Date of Patent: Feb. 3, 2004

(54) HEADSET EAR SEAL

(75) Inventor: Allan E. Sheppard, Jr., Holden, MA (US)

(73) Assignee: David Clark Company Incorporated, Worcester, MA (US)

( * ) Notice: Subject to any disclaimer, the term of this patent is extended or adjusted under 35 U.S.C. 154(b) by 0 days.

(21) Appl. No.: 10/121,987

(22) Filed: Apr. 12, 2002

(51) Int. Cl.⁷ .......................... H04R 25/00; G10K 11/00
(52) U.S. Cl. ........................ 181/129; 151/128; 151/126
(58) Field of Search ................................. 181/129, 126, 181/128, 198

(56) References Cited

U.S. PATENT DOCUMENTS

| | | | |
|---|---|---|---|
| 2,408,494 A | 10/1946 | Ueneklasen | |
| 2,989,274 A | 6/1961 | Moran | |
| 3,571,813 A | 3/1971 | Allen | 2/209 |
| 3,593,341 A | 7/1971 | Aileo | |
| 3,944,018 A * | 3/1976 | Satory | 181/175 |
| 4,403,120 A | 9/1983 | Yoshimi | 179/182 |
| 4,455,675 A | 6/1984 | Bose et al. | 281/74 |
| 4,523,661 A | 6/1985 | Scalzo et al. | 181/129 |
| 4,572,323 A | 2/1986 | Randall | 181/129 |
| 4,644,581 A | 2/1987 | Sapiejewski | 381/74 |
| 4,674,134 A | 6/1987 | Lundin | 2/209 |
| 4,674,137 A | 6/1987 | Girse | 4/255 |
| 4,689,822 A | 8/1987 | Houng | 381/183 |
| 4,830,138 A * | 5/1989 | Palmaer et al. | 181/129 |
| 4,856,118 A * | 8/1989 | Sapiejewski | 2/209 |
| 4,857,118 A | 8/1989 | Van Mens et al. | 148/103 |
| 4,922,542 A | 5/1990 | Sapiejewski | 281/187 |
| 4,944,361 A | 7/1990 | Lindgren et al. | 181/129 |
| 4,989,271 A * | 2/1991 | Sapiejewski et al. | 2/209 |
| 5,020,163 A | 6/1991 | Aileo et al. | 2/209 |
| D326,855 S | 6/1992 | Bose et al. | D14/223 |
| 5,138,722 A | 8/1992 | Urella et al. | 2/209 |
| 5,148,887 A | 9/1992 | Murphy | 181/129 |
| 5,185,807 A | 2/1993 | Bergin et al. | 381/183 |
| 5,208,868 A | 5/1993 | Sapiejewski | 381/83 |
| 5,243,709 A | 9/1993 | Sheehan et al. | 2/209 |
| 5,276,740 A | 1/1994 | Inanaga et al. | 281/187 |
| D344,611 S | 2/1994 | Hordis | D29/19 |
| 5,293,647 A | 3/1994 | Mirmilshteyn et al. | 2/209 |
| 5,295,366 A | 3/1994 | Lopez et al. | 62/266 |
| 5,305,387 A | 4/1994 | Sapiejewski | 381/71 |
| 5,361,304 A | 11/1994 | Jones et al. | 281/72 |
| 5,402,497 A | 3/1995 | Nishimoto et al. | 381/95 |
| 5,497,427 A | 3/1996 | Nageno | 381/183 |
| 5,555,554 A | 9/1996 | Hofer et al. | 381/183 |
| 5,590,213 A | 12/1996 | Urella et al. | 381/183 |
| D391,575 S | 3/1998 | Bergin et al. | D14/223 |
| D398,309 S | 9/1998 | Bergin et al. | D14/206 |
| 5,821,468 A | 10/1998 | Urella et al. | 181/129 |
| 5,911,314 A | 6/1999 | Urella et al. | 2/209 |
| 5,920,911 A * | 7/1999 | Cushman | 2/209 |
| D415,763 S | 10/1999 | Petchonka | D14/205 |
| 5,970,160 A | 10/1999 | Nilsson et al. | 381/371 |
| 5,996,123 A | 12/1999 | Leight et al. | 2/209 |
| 6,091,825 A | 7/2000 | Minkofski | 381/72 |
| 6,163,615 A | 12/2000 | Callahan | 381/371 |
| 6,236,969 B1 | 5/2001 | Ruppert et al. | 704/275 |
| 6,295,366 B1 | 9/2001 | Haller et al. | 381/374 |
| 6,333,982 B1 | 12/2001 | Sapiejewski et al. | 379/430 |

FOREIGN PATENT DOCUMENTS

GB 900681 * 7/1962 ............... 181/129

* cited by examiner

*Primary Examiner*—Robert Nappi
*Assistant Examiner*—Patrick Miller
(74) *Attorney, Agent, or Firm*—Samuels Gauthier & Stevens

(57) ABSTRACT

An ear seal is disclosed for use in a headset. The ear seal includes a flexible sheath that encloses and is in contact with flowable material. The flexible sheath includes a first surface that extends between inner and outer peripheral edges of an annular top. The first surface is adapted for contacting a user's head and includes an inner annular groove separating an inner annular surface portion from a crease inhibiting central annular surface portion, and an outer annular groove separating an outer annular surface portion from the crease inhibiting central annular surface portion.

11 Claims, 2 Drawing Sheets

HEADSET EAR SEAL

BACKGROUND OF THE INVENTION

The invention relates to headsets having ear domes adapted to attenuate noise. Such headsets may be used with communication equipment as well as ear protectors and other similar noise attenuating devices. The invention particularly relates to ear seals for use with such headsets.

Headsets typically function by enclosing the ears of a user within earcups such as plastic domes. Comfortable ear seals are interposed between the earcups and the user's head to assist in isolating the ears from offending noise originating outside the earcups. The earcups are typically attached to a spring and suspension assembly that applies a force urging the ear seals in place against the head of a user. The difficulty in providing improved noise attenuation without detracting from comfort has been long recognized. See for example, U.S. Pat. Nos. 6,163,615; 5,293,647; 4,944,361; 3,571,813 and 2,408,494.

The ear seals that are interposed between the earcups and the user's head are known to be formed of a variety of foam materials, including sponge plastic and foam rubber (see U.S. Pat. No. 3,593,341), highly compliant foam (see U.S. Pat. No. 4,922,542), polyurethane foam (see U.S. Pat. Nos. 4,958,697, 5,020,163 and 5,148,887) and scythed urethane foam (see U.S. Pat. No. 6,295,366). Ear seals made of these foam materials are known to be formed in a variety of shapes.

Flowable materials such as liquids and semi-solids are also known to be used in ear seals by enclosing the flowable material in a flexible sealed enclosure. Conventional flowable materials used in such ear seals include liquid glycerine (See U.S. Pat. No. 4,674,134), nonliquid silicone gel (see U.S. Pat. No. 4,856,118), and a liquid mixture of dilatent silicone compound and a silicone oil (see U.S. Pat. Nos. 5,138,722, 5,911,314 and 5,821,468). Although the foam material is known to be formable into a variety of shapes, flexible sealed enclosures for containing flowable material have typically been formed as pliable annular rings that may closely conform to a users head.

It has been found that foam ear seals do not sufficiently exclude ambient noise in certain applications, and ear seals including a flowable material within a flexible sealed enclosure may permit a small amount of ambient noise to enter the dome cavity in certain situations. For example, during use a flexible sealed enclosure may develop creases in the surface that contacts a user's head. If any of these creases extend from within the ear dome cavity to the outer peripheral edge of the ear seal, then such creases may form channels through which ambient noise may enter the ear dome cavity compromising noise attenuation.

It is conventionally believed that the material used for the flexible sealed enclosure should be thin, soft and pliable so as to adjust itself well to the shape of a user's head. See for example, U.S. Pat. No. 4,674,134. It is also conventionally believed that if the exposed surface of the ear seal is irregularly shaped, any irregularities in the shape should be constrained from unwanted irreversible movement. For example, although U.S. Pat. Nos. 4,856,118 and 4,989,271 disclose the use of two concentric annular cavities for containing a silicone gel, U.S. Pat. No. 4,989,271 discloses that the base of the groove between the concentric annular cavities should be sealed to an inner ring to prevent the groove from inverting due to undesired movement of the gel during use. Such ear seals including two separately secured annular cavities for containing silicone gel, however, have not been found to provide sufficient noise attenuation in certain applications.

There is a need, therefore, for an improved ear seal for headsets that provides sufficient noise attenuation and comfort.

SUMMARY OF THE INVENTION

The invention provides an ear seal for use in a headset. The ear seal includes a flexible sheath that encloses and is in contact with flowable material. The flexible sheath includes a first surface extending between inner and outer peripheral edges of an annular top. The first surface is adapted for contacting a user's head and includes an inner annular groove separating an inner annular surface portion from a crease inhibiting central annular surface portion, and an outer annular groove separating an outer annular surface portion from the crease inhibiting central annular surface portion.

BRIEF DESCRIPTION OF THE ILLUSTRATED EMBODIMENT

The following description may be further understood with reference to the accompanying drawings in which.

The drawings are shown for illustrative purposes only and are not to scale.

DETAILED DESCRIPTION OF THE ILLUSTRATED EMBODIMENT

It has been discovered that noise attenuation may be improved in an ear seal containing a flowable material by providing an outer surface of the ear seal with a crease inhibiting central annular surface that is separated from inner and outer annular surfaces by a plurality of annular grooves. Creases initiating from within the dome cavity and from outside the dome cavity are inhibited from traversing the outer surface of the ear seal due to presence of a plurality of annular grooves having a particular geometry.

Figure 1:
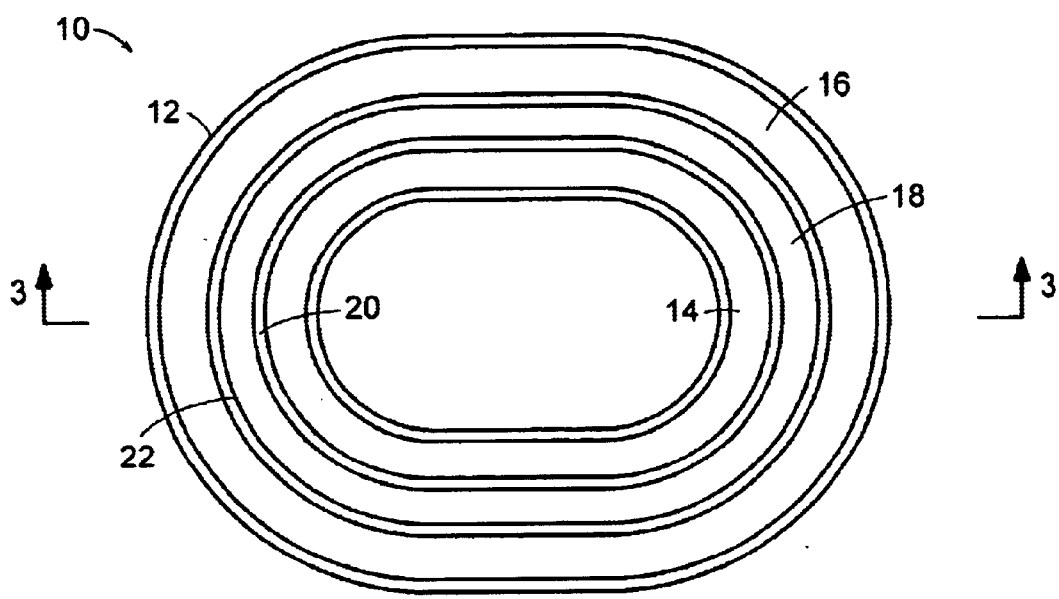
FIG. 1 shows an illustrative top plan view of an ear seal in accordance with an embodiment of the invention.
Figure 2:
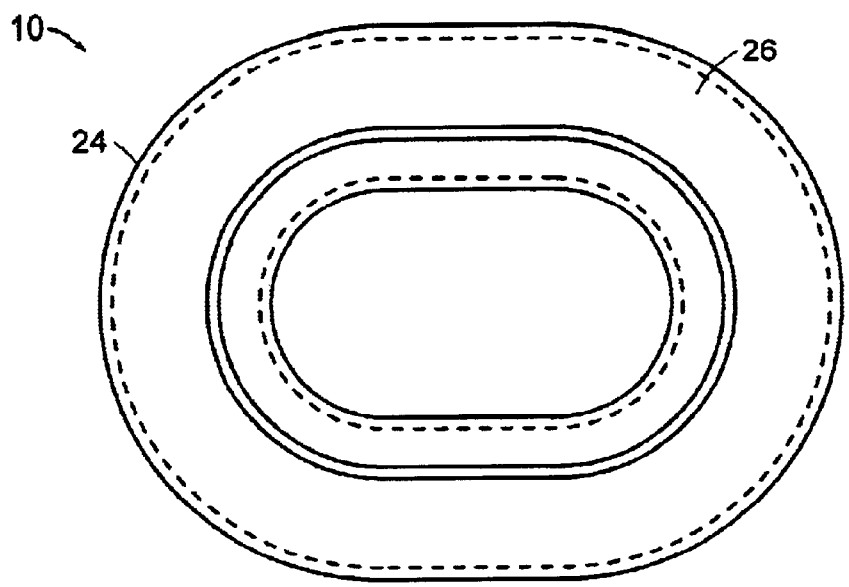
FIG. 2 shows an illustrative bottom plan view of the ear seal shown in FIG. 1.
Figure 3:
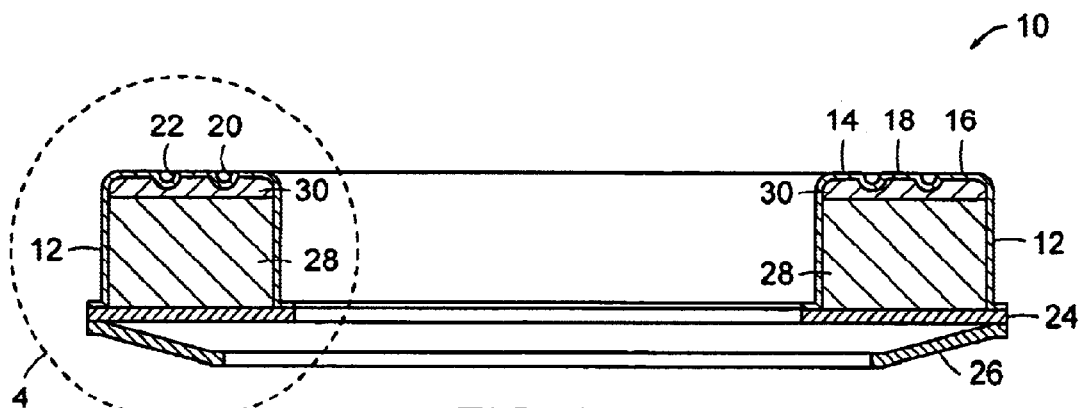
FIG. 3 shows an illustrative sectional view of the ear seal shown in FIG. 1 taken along line 3—3 thereof.
Figure 4:
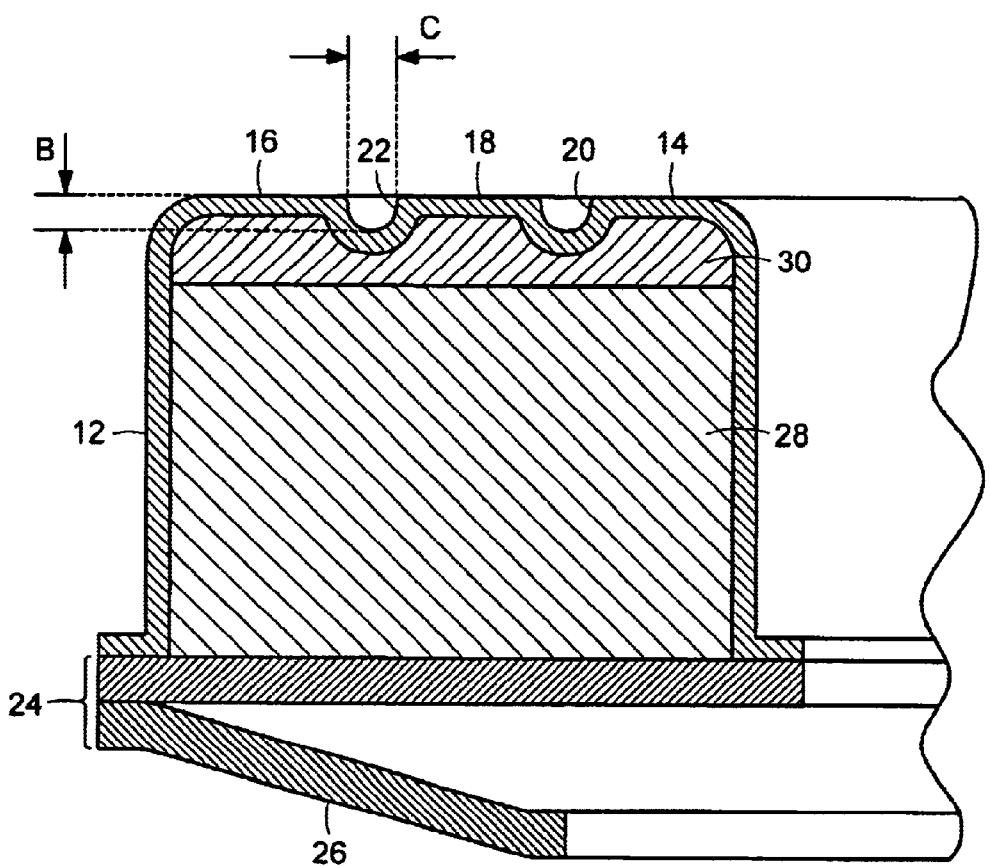
FIG. 4 shows a portion of the illustrated section view shown in FIG. 3 as generally indicated at A in an enlarged scale.

In particular, as shown in FIG. 1, an ear seal 10 in accordance with an embodiment of the invention includes an annular top having a flexible sheath 12 that includes an inner annular surface portion 14, an outer annular surface portion 16 and a crease inhibiting central annular surface portion 18. The inner annular surface portion 14 is separated from the crease inhibiting central annular surface portion 18 by an inner annular groove 20, and the outer annular surface portion 16 is separated from the crease inhibiting central annular surface portion 18 by an outer annular groove 22. As shown in FIGS. 2–4, the ear seal 10 also includes an annular base 24 having an annular flap 26 for engaging an annular lip on a headset dome.

As shown in FIGS. 3 and 4, the annular top further includes a foam insert material 28 and a flowable material 30 enclosed within the flexible sheath 12. The foam insert material 28 is preferably a slow recovery polyurethane foam, and the flowable material 30 is preferably a liquid combination of a dilatent silicone compound and silicone oil. The flexible sheath may be formed of polyurethane having a thickness of about 0.005 inches to about 0.05 inches and is preferably about 0.0165 inches. The foam material 28 may be about 0.25 inches to about 0.75 inches and is preferably about 0.5 inches, and the depth of the flowable material may be about 0.05 inches to about 0.20 inches and is preferably about 0.10 inches. The grooves 20 and 22 may have depths (as indicated at B in FIG. 4) of about 0.01 to about 0.30 inches and are preferably about 0.05 inches. The grooves 20 and 22 may have widths (as indicated at C in FIG. 4) of about 0.01 inches to about 0.10 inches and are preferably about 0.062 inches. The width of each annular side of the ear seal may be between 0.5 inches to about 1.25 inches and is preferably about 0.75 inches, and the width of each inner, outer and central surfaces may be about 0.2 inches.

The depth of each of the grooves, therefore, is preferably about ½ the thickness of the flowable material, and the thickness of the flowable material is preferably about ⅓ the thickness of the foam material. The depth of each of the grooves is also preferably about four times the thickness of the flexible sheath. The width of each of the grooves is preferably slightly greater than the depth of the grooves and less than the thickness of the flexible sheath. The width of each of the grooves is also preferably less than about 10% of the width of each annular side of the ear seal.

It has been found that during use, the central annular surface as defined by grooves in accordance with the above embodiments inhibits creases initiating from within the dome cavity and from outside the dome cavity from traveling across the outer surface of the ear seal.

Those skilled in the art will appreciate that numerous modifications and variations may be made to the above disclosed embodiments without departing from the spirit and scope of the invention.

What is claimed is:

1. An ear seal for use in a headset, said ear seal comprising a flexible sheath in contact with and enclosing a flowable material, said flexible sheath providing a first surface extending between inner and outer peripheral edges of an annular top, said first surface being adapted for contacting a user's head and including an inner annular groove separating an inner annular surface portion from a crease inhibiting central annular surface portion, and an outer annular groove separating an outer annular surface portion from said crease inhibiting central annular surface portion.

2. The ear seal as claimed in claim 1, wherein each of said inner and outer annular grooves has a depth of about 0.05 inches deep.

3. The ear seal as claimed in claim 1, wherein each of said inner and outer annular grooves has a depth of less than about 0.10 inches deep.

4. The ear seal as claimed in claim 1, wherein said inner and outer grooves have a depth and a width, and the width is greater than the depth of each of the grooves and greater than a thickness of the flexible sheath.

5. An ear seal for use in a headset, said ear seal comprising:
   an annular base providing a first surface extending between inner and outer peripheral edges of said annular base, said first surface being adapted for securing said ear seal to the headset;
   an annular foam ring adjacent said annular base;
   an annular top including a flexible sheath providing a second surface extending between inner and outer peripheral edges of said annular top, said second surface being adapted for contacting a user's head and including an inner annular surface portion, an outer annular surface portion, a crease inhibiting central annular surface portion, an inner annular groove separating said inner annular surface portion from said crease inhibiting annular surface portion, and an outer annular groove separating said outer annular surface portion from said crease inhibiting annular surface portion; and
   a flowable material that is captured between said foam ring and said flexible sheath.

6. The ear seal as claimed in claim 5, wherein each of said inner and outer annular grooves has a depth of about 0.05 inches deep.

7. The ear seal as claimed in claim 5, wherein each of said inner and outer annular grooves has a depth of less than about 0.10 inches deep.

8. The ear seal as claimed in claim 5, wherein said inner and outer grooves have a depth and a width, and the width is greater than the depth of each of the grooves and greater than a thickness of the flexible sheath.

9. The ear seal as claimed in claim 5, wherein a width of each of said inner and outer grooves is less than about 10% of a width of each annular side of the ear seal.

10. An ear seal for use in a headset, said ear seal comprising an exposed surface for contacting a head of a user and including a flexible sheath enclosing a flowable material and providing a first surface extending between inner and outer peripheral edges of said annular top, said first surface including:
    an inner annular surface portion having a first width;
    an outer annular surface portion having a second width;
    a crease inhibiting central annular surface portion having a third width;
    an inner annular groove separating said inner annular surface portion from said crease inhibiting annular surface portion, said inner annular groove having a fourth width that is about ⅓ the width of each of said first, second and third widths;
    an outer annular groove separating said outer annular surface portion from said crease inhibiting annular surface portion, said outer annular groove having a fifth width that is about ⅓ the width of each of said first second and third widths.

11. The ear seal as claimed in claim 10, wherein said inner and outer grooves each have a depth that is less than about 0.10 inches deep.

* * * * *